United States Patent
Tanaka et al.

(10) Patent No.: US 7,156,553 B2
(45) Date of Patent: *Jan. 2, 2007

(54) PORTABLE RADIATION IMAGING SYSTEM AND A RADIATION IMAGE DETECTION DEVICE EQUIPPED WITH AN ANGULAR SIGNAL OUTPUT MEANS

(75) Inventors: Hiroshi Tanaka, Kaisei-machi (JP); Kazuo Shimura, Kaisei-machi (JP); Takeshi Ohkubo, Kaisei-machi (JP)

(73) Assignee: Fuji Photo Film Co., Ltd., Kanagawa-ken (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/959,510

(22) Filed: Oct. 7, 2004

(65) Prior Publication Data

US 2005/0058244 A1    Mar. 17, 2005

Related U.S. Application Data

(63) Continuation of application No. 09/987,654, filed on Nov. 15, 2001, now Pat. No. 6,890,099.

(30) Foreign Application Priority Data

Nov. 15, 2000   (JP)   ............................ 2000-348002

(51) Int. Cl.
*H05G 1/02*   (2006.01)

(52) U.S. Cl. ..................................... 378/205; 378/116

(58) Field of Classification Search ........ 378/205–207, 378/170, 98.8, 116; 250/303, 203–203.1, 250/203.2, 370.08, 370.09
See application file for complete search history.

(56) References Cited

U.S. PATENT DOCUMENTS

| | | | |
|---|---|---|---|
| 4,258,264 A | 3/1981 | Kotera et al. | |
| 4,617,681 A | 10/1986 | LaFiandra et al. | |
| 4,894,855 A | 1/1990 | Kresse | |
| 5,113,424 A | 5/1992 | Burdea et al. | |
| 5,734,694 A | 3/1998 | Khutoryansky et al. | |
| 5,835,558 A | 11/1998 | Maschke | |
| 5,940,470 A | 8/1999 | Palm-Plessmann et al. | |
| 6,072,188 A | 6/2000 | Arakawa | |
| 6,106,152 A * | 8/2000 | Thunberg | 378/205 |
| 6,142,667 A | 11/2000 | Pattee | |
| 6,196,715 B1 | 3/2001 | Nambu et al. | |

(Continued)

FOREIGN PATENT DOCUMENTS

JP    55-12429    1/1980

(Continued)

*Primary Examiner*—Courtney Thomas
*Assistant Examiner*—Hoon Song
(74) *Attorney, Agent, or Firm*—Sughrue Mion, PLLC

(57) ABSTRACT

A portable radiation imaging system is provided which is capable of always performing imaging in a state where the tilt of the radiation emitted from a radiation source in relation to the detection surface of an image detection device is substantially perpendicular. The system is equipped with a tilt adjustment means that makes the tilt of the radiation in relation to the detection surface of a radiation image detection device substantially perpendicular by changing the tilt angle of a radiation source based on an angular signal representing the degree of tilt of the radiation in relation to said detection surface output by an angular signal output means, and a command means that generates an exposure command to the radiation source when the tilt of the radiation to be emitted from said radiation source in relation to the detection surface of said radiation image detection device is substantially perpendicular.

34 Claims, 5 Drawing Sheets

U.S. PATENT DOCUMENTS

| | | |
|---|---|---|
| 6,200,024 B1 * | 3/2001 | Negrelli .................... 378/197 |
| 6,302,580 B1 | 10/2001 | Dwyer, Jr. et al. |
| 6,325,537 B1 | 12/2001 | Watanabe |
| 6,412,978 B1 | 7/2002 | Watanabe et al. |
| 6,422,750 B1 * | 7/2002 | Kwasnick et al. .......... 378/205 |
| 6,435,715 B1 | 8/2002 | Betz et al. |
| 6,439,769 B1 | 8/2002 | Polkus et al. |
| 6,890,099 B1 * | 5/2005 | Tanaka et al. .............. 378/205 |
| 6,893,157 B1 * | 5/2005 | Arakawa .................... 378/205 |

FOREIGN PATENT DOCUMENTS

| | | |
|---|---|---|
| JP | 56-11395 | 2/1981 |
| JP | 3-295540 | 12/1991 |

\* cited by examiner

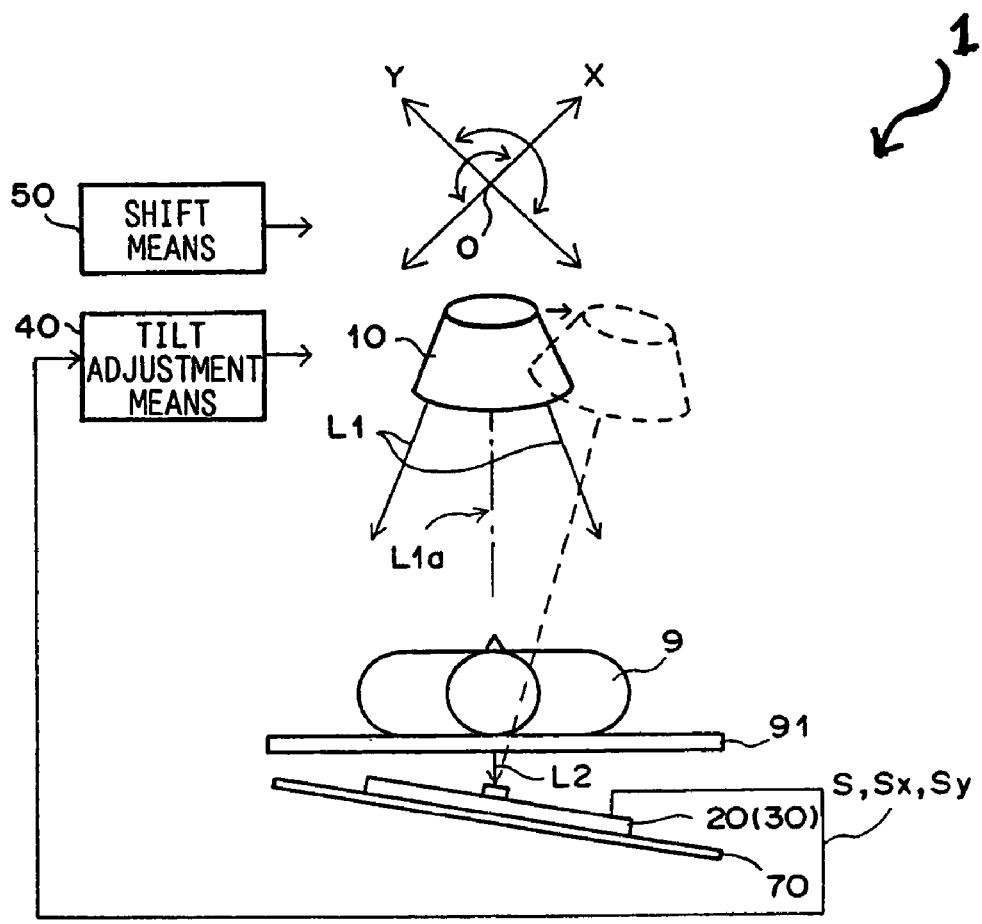

F I G . 3
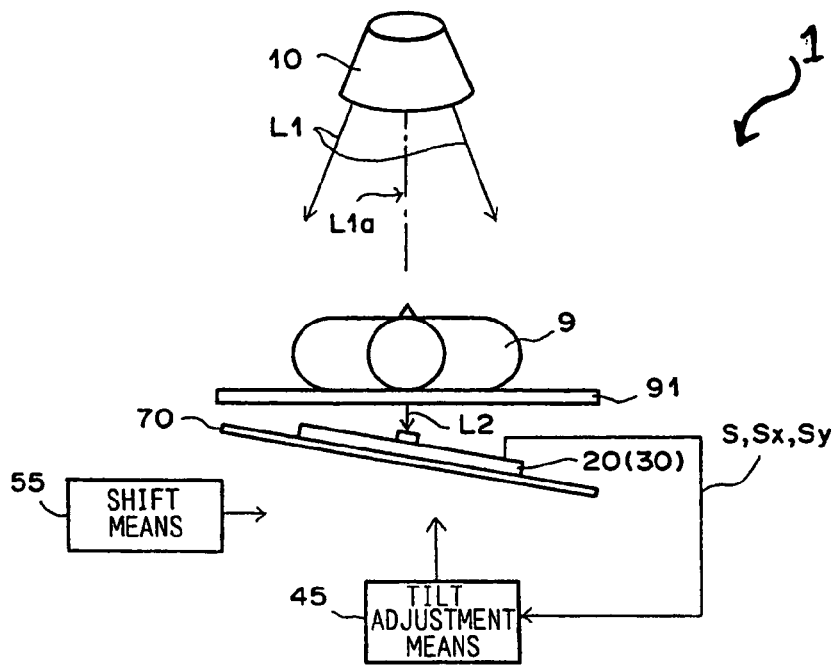
F I G . 4
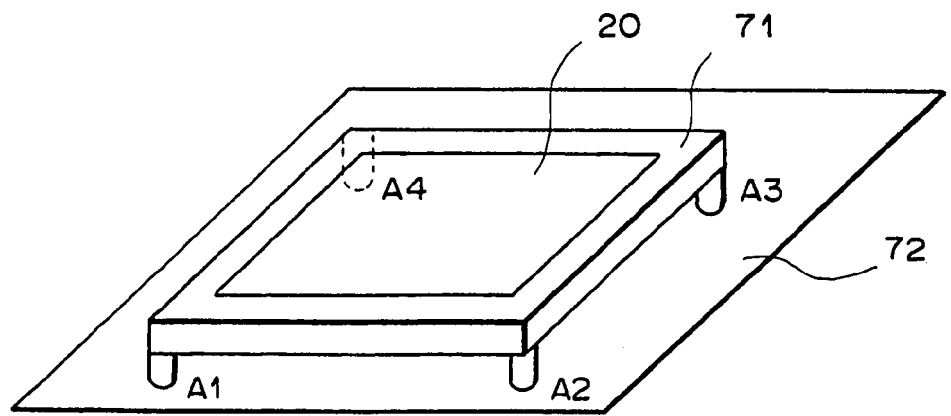

F I G . 5
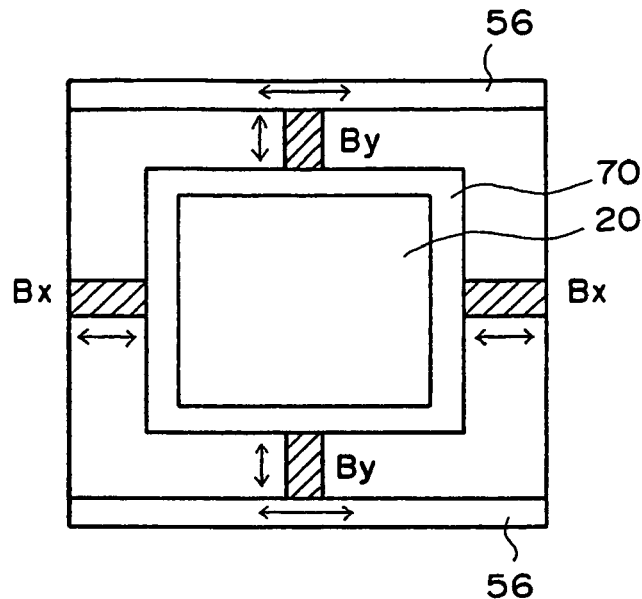
F I G . 6
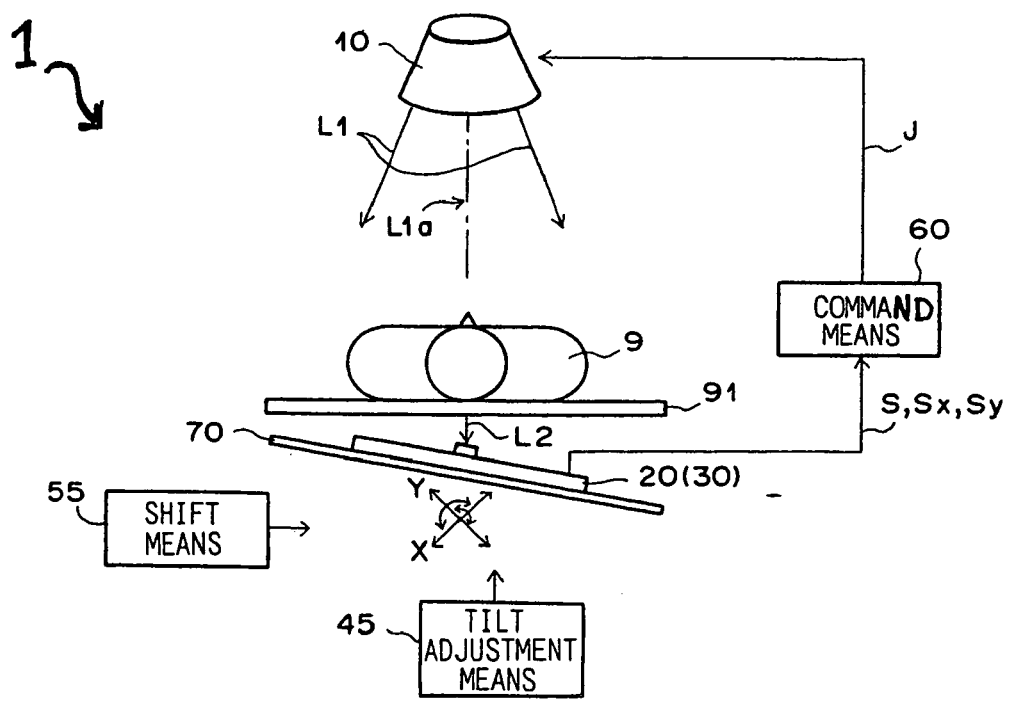

PORTABLE RADIATION IMAGING SYSTEM AND A RADIATION IMAGE DETECTION DEVICE EQUIPPED WITH AN ANGULAR SIGNAL OUTPUT MEANS

This is a continuation of application Ser. No. 09/987,654 filed Nov. 15, 2001 now U.S. Pat. No. 6,890,099.

BACKGROUND OF THE INVENTION

1. Field of the Invention

The present invention relates to a portable radiation imaging system and a radiation image detection device for said imaging system.

2. Description of the Related Art

Apparatuses for forming radiation images, constituting a radiation source and a radiation image detection device, such as X-ray imaging systems and CR systems (as disclosed in, for example, Japanese Unexamined Patent Publication No. 55(1980)-12429 and Japanese Unexamined Patent Publication No. 56(1981)-11395 by the present applicant, etc.) are widely used in the medical field.

Today, use of the aforementioned systems is not limited to the imaging rooms of hospitals (treatment settings). Said systems are being brought into the ICU ward to take a plurality of images in a short time span, or brought out to patients and other people desiring treatment outside the hospital and imaging performed at these settings. Systems that can be carried and transported in this manner will be referred to hereinafter as portable radiation imaging systems (as disclosed in Japanese Unexamined Patent Publication No. 3(1991)-295540.

Meanwhile, to obtain a radiation image appropriate for use in diagnosis, it is necessary to maintain the relative angle between a cassette or the like which houses an image recording medium such as X-ray film or an imaging plate and the radiation source (tubular bulb) substantially perpendicular. More specifically, it is said that it is necessary to maintain the angle between the radiation emitted from the radiation source and the detection surface of the image detection device such as the aforementioned cassette or the like substantially perpendicular. This is in order to prevent the occurrence of false images in the case that, for example, a scattered ray removal grid board is utilized, and also for reasons of image reproducibility.

However, in the case that a portable radiation imaging system is utilized in, for example, an ICU ward to take many images within a short period of time, it is not possible to maintain the angle between the cassette and the radiation source perpendicular. As the angle changes for each image, diagnosis utilizing the obtained images becomes difficult. The same problem arises in the case that the system is brought outside the hospital to perform imaging in an alternate setting.

SUMMARY OF THE INVENTION

The present invention has been made in view of the above-described circumstances, and it is a primary object of the invention to provide a portable radiation imaging system that is capable of performing imaging in a state in which the angle between the radiation emitted from the radiation source and the detection surface of the image detection device is substantially perpendicular at all times.

It is another object of the present invention to provide a radiation image detection device to be utilized by the radiation imaging system of the present invention.

The first radiation imaging system according to the present system is a portable radiation imaging system constituting a radiation source and a two-dimensional radiation image detection device that records a radiation image by detecting the radiation that has been transmitted through a subject. The system is characterized by being further equipped with an angular signal output means that outputs an angular signal which represents the tilt angle between the radiation emitted from the radiation source and the detection surface of the image detection device, and an tilt adjustment means that changes the tilt angle of the radiation source based on the angular signal output from said angular signal output means so that the angle between the radiation emitted from the radiation source and the detection surface of the image detection device becomes substantially perpendicular.

In other words, the first radiation imaging system of the present invention is of a type that adjusts the angle between the radiation source and the detection surface of the radiation image detection device by changing the angle on the radiation source side.

The second radiation imaging system according to the present invention is a portable radiation imaging system constituting a radiation source and a two-dimensional radiation image detection device that records a radiation image by detecting the radiation that has been transmitted through a subject. The system is characterized by being further equipped with an angular signal output means that outputs an angular signal which represents the tilt angle between the radiation emitted from the radiation source and the detection surface of the image detection device, and an tilt adjustment means that changes the tilt angle of the radiation image detection device based on the angular signal output from said angular signal output means so that the angle between the radiation emitted from the radiation source and the detection surface of the image detection device becomes substantially perpendicular.

In other words, the second radiation imaging system of the present invention is of a type that adjusts the angle between the radiation source and the detection surface of the radiation image detection device by changing the angle on the radiation image detection device side.

The third radiation imaging system according to the present invention is a portable radiation imaging system constituting a radiation source and a two-dimensional radiation image detection device that records a radiation image by detecting the radiation that has been transmitted through a subject. The system is characterized by being further equipped with a command means for generating an exposure command to the radiation source when the angle between the radiation emitted therefrom and the detection surface of the radiation image detection device is substantially perpendicular.

In other words, the third radiation imaging system of the present invention is of a type that automatically generates an exposure command at a point when the angle between the radiation to be emitted from the radiation source and the detection surface of the radiation image detecting device is made to be substantially perpendicular by adjusting the tilt on either the radiation source side or the radiation image detection device side.

Further, this third system can be combined with the first or second systems. That is, it can be of a structure equipped with a tilt adjustment means for changing either the tilt angle on the radiation source side or the radiation image detection device side. Note that the changing of the tilt on the radiation source side or the radiation image detection device side may be a manual operation.

With regard to the first through third radiation systems described above, it is preferable that they be further equipped with a portable shift means for moving either the radiation source or the radiation image detection device horizontally.

To enable horizontal movement of either the radiation source or the radiation image detection device means that both or one of these elements becomes capable of motion relative to the other. The object of such structure is to make positional adjustments possible so that the after either the radiation source or the radiation image detection device is tilted, the central axis of the radiation emitted from the radiation source can be adjusted to be positioned to the substantially central portion of the detecting surface of the radiation image detection device or to the vicinity of a target area of a subject. To this end, it does not matter if the distance between the radiation source and the radiation image detection device (the distance along the central axis of the radiation) changes. For example, it is possible to move the radiation source laterally (the axial distance changes) or to move the radiation source in a parallel direction in relation to the detection surface of the radiation image detection device (the axial distance does not change)

The first radiation image detecting device according to the present invention is a two-dimensional radiation image detecting device capable of recording a radiation image. Said device is characterized by being equipped with an angular signal output means that outputs an angular signal which represents the tilt angle between the radiation emitted from the radiation source and the detection surface of the image detection device, and is especially suited for use with the first or second radiation imaging system described above.

The second radiation image detection device according to the present invention is a two-dimensional radiation image detecting device capable of recording a radiation image. Said device is characterized by being equipped with a command means for generating an exposure command to the radiation source when the angle between the radiation emitted therefrom and the detection surface of the radiation image detection device is substantially perpendicular, and is especially suited for use with the third radiation imaging system described above.

With regard to the above, a two-dimensional radiation image detection device refers to a device capable of recording a radiation image in a two-dimensional form.

With regard to this detection device, X-ray film, stimulable phosphor sheets (imaging plate) or the like, for example may be utilized as the image recording medium. Or, a solid state radiation detection device utilizing semiconductors (static electricity recording medium) as disclosed in Japanese Unexamined Patent Publication Nos. 9(1997)-206293 and 9(1997)-321267 or Japanese Unexamined Patent Publication No. 2000-105297, for example, may be utilized as the image recording medium. Also, the image recording medium may be housed in a cassette and utilized. Further, the radiation image detection device may be provided with a grid board to remove the scattered rays generated by the subject.

With regard to the above, the tilt angle between the radiation emitted from the radiation source and the detection surface of the radiation image detecting device refers to the angle formed by the central axis of said radiation and the line normal to the detection surface of said radiation image detecting device, that is, the incidence angle of the central axis of the radiation in relation to said detection surface.

As the angular signal output means that outputs an angular signal representing this tilt angle, any means that can detect said tilt angle may be utilized. For example, an instrument that measures levelness such as an electronic level, or an instrument that measures angle such as a projection style angle sensor may be utilized.

Although it is stated that the tilt of the radiation in relation to the detection surface of the radiation image detection device is made to be substantially perpendicular, it is not necessary that said tilt be strictly perpendicular. It is sufficient to make the tilt approximately perpendicular to a grid board or an image recording medium, etc., that is to maintain a perpendicular relationship therewith according to the system structure.

The first or second radiation imaging apparatuses of the present invention, in combination with the first radiation image detection device, are structured to change the tilt of the radiation source or the image detection device according to the degree of tilt therebetween and adjusting said tilt to become substantially perpendicular. Accordingly, imaging is always performed in a state where the angle of the radiation in relation to the detection surface is substantially perpendicular, and an image suitable for use in diagnosis can be obtained.

The third radiation imaging apparatus of the present invention, in combination with the second radiation image detection device, are structured to generate an exposure command at a point when the central axis of the radiation is substantially perpendicular to the detection surface. Accordingly, imaging is always performed in a state where the angle of the central axis of the radiation in relation to the detection surface is substantially perpendicular, and an image suitable for use in diagnosis can be obtained.

BRIEF DESCRIPTION OF THE DRAWINGS

FIG. 1 is a schematic view that shows the structure of the first embodiment of the radiation imaging system of the present invention.

FIG. 3 is a schematic view that shows the structure of the second embodiment of the radiation imaging system of the present invention.

FIG. 4 shows an example of a tilt adjusting means.

FIG. 5 shows an example of a shift means.

FIG. 6 is a schematic view that shows one example of a structure for the third embodiment of the radiation imaging system of the present invention.

DESCRIPTION OF THE PREFERRED EMBODIMENTS

Hereinafter, the embodiments of the present invention will be described in detail with reference to the drawings.

Figure 2A:
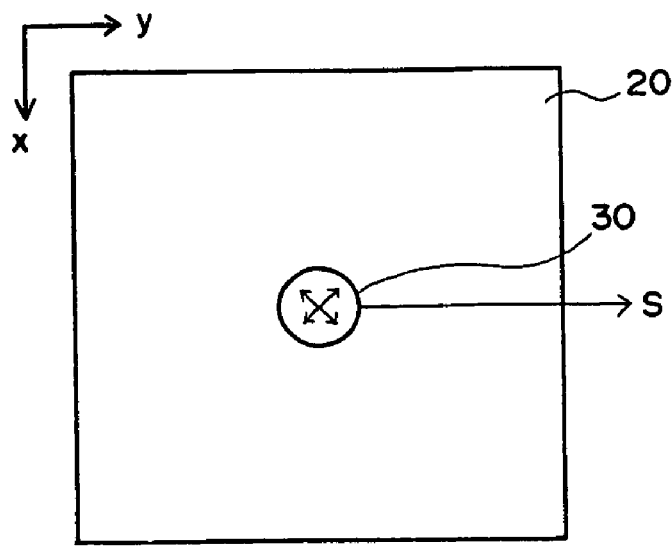
FIG. 2A and FIG. 2B are schematic views that show the radiation image detection device.
Figure 2B:
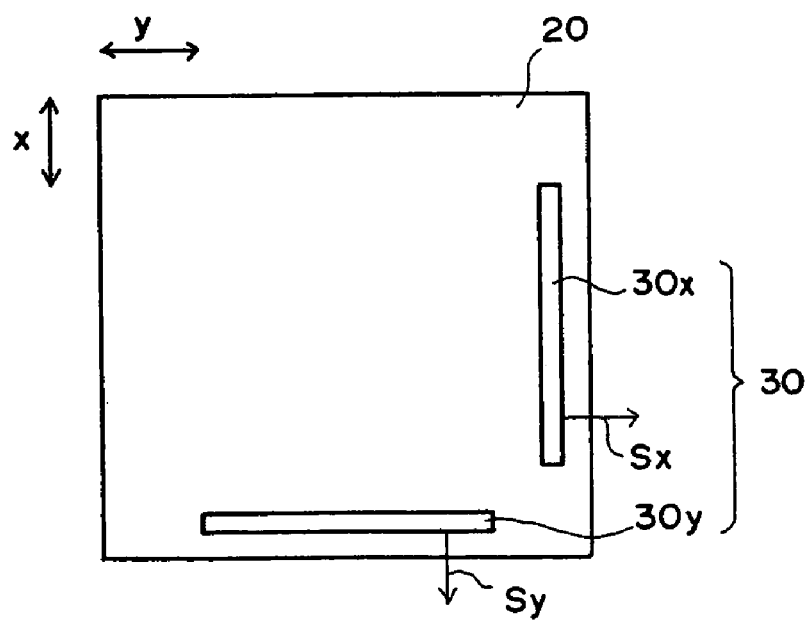

FIG. 1 is a schematic view that shows the structure of the first embodiment of the radiation imaging system of the present invention, and FIGS. 2A and 2B are schematic views that show the radiation image detection device.

The first embodiment of the radiation imaging system shown in FIG. 1 is a portable system of the type that adjusts the angle between the central axis of the radiation and the detection surface of the radiation image detection device to become perpendicular by changing the tilt on the radiation source side. It will be described in detail below.

As shown in FIG. 1, the first embodiment of the radiation imaging system 1 comprises: a radiation source 10 that emits radiation L1; and a two dimensional radiation image detection device that records a radiation image by detecting the radiation L2 which has passed through a subject 9 after being emitted from said radiation source 10. The radiation source 10 and the radiation image detection device 20 are structured to be carriable. Although not shown in the figure, it is preferable to provide a sensor that detects the horizontal position of the center of either the detection device 20 or the subject 9.

The system 1 is further equipped with: an angular signal output means 30 that outputs an angular signal which represents the tilt angle between the radiation L1 emitted from the radiation source 10 and the detection surface of radiation image detection device 20; a tilt adjustment means 40 that changes the tilt angle of the radiation source based on the angular signal output from said angular signal output means so that the angle between the radiation emitted from the radiation source and the detection surface of the image detection device becomes substantially perpendicular; and a shift means 50 that enables horizontal movement of the radiation source 10. It need not be said that angular signal output means 30, the tilt adjustment means 40, as well as the shift means 50 are to be structured so as to be portable.

The subject 9 is placed on a support 91, such as a stretcher or a bed, positioned between the radiation source 10 and the image detection device 20. The image detection device 20 is placed on a holding member 70, which is slightly larger than said image detection device 20.

As to the image detection device, one may be utilized which has a stimulable phosphor sheet or a solid state radiation detection device housed with in a cassette having a grid provided on the detection surface side facing the radiation source 10 thereof to prevent scattered rays, for example.

With regard to the structure of the first embodiment, the angular signal output means 30 is equipped integrally with the radiation image detection device 20. Specifically, as shown in FIGS. 2A and 2B, the angular signal output means 30 is provided on a surface (either the detection surface or the reverse surface) or on a side of the radiation image detection device. As to the angular signal output means 30, an electronic level that is capable of outputting an angular signal S representing two dimensional tilt (degree of levelness) utilizing one sensor as shown in FIG. 2A maybe used, for example. Or, the angular signal output means 30 can be composed of an electronic level 30x capable of outputting an angular signal Sx representing tilt (tilt in relation to a horizontal plane) in an x direction and an electronic level 30y capable of outputting an angular signal Sy representing tilt (tilt in relation to a vertical plane) in a y direction as shown in FIG. 2B. The two dimensional tilt (degree of levelness) can be recognized by the two angular signals Sx and Sy.

In either structure, the detected angular signal S or Sx and Sy is input to the tilt adjustment means 40.

As shown in FIG. 1, as the structure of the shift means 50, one is adopted which is capable of moving the radiation source 10 in the X as well as the Y directions. As to the structure of the tilt adjustment means 40, one is adopted which is independently rotatable in the X and Y directions to enable tilting in both the X-Y planes. To this end, it does not matter what specific means are utilized. By such a structure, the tilt of the central axis L1a of radiation L1 emitted from radiation source 10 in relation to the detection surface of image detection device 20 becomes adjustable, and the shift between said central axis L1a and the center of the subject 9 or the center of detection device 20 also becomes adjustable.

The angular signal detected by the angular signal output means 30 is input into tilt adjustment means 40. The tilt adjustment means 40 changes the tilt angle of the radiation source 10 based on said angular signal input thereto, thereby making substantially perpendicular the tilt of the radiation L1 in relation to the detection surface of the image detection device 20. Specifically, the radiation source 10 is tilted to correct the horizontal shift of the detection surface of image detection device 20.

Note that if the tilt angle of radiation source 10 is changed, the relative position between the central axis L1a of radiation L1 emitted from radiation source 10 and the radiation image detection device 20 or the subject 9 in the horizontal direction shifts. The amount of this shift increases as the tilt angle of radiation source 10 increases, and there are some cases in which a subject image cannot be recorded. To avoid this, the shift means 50 moves the radiation source 10 in a horizontal direction so that the central axis L1a of radiation L1 is positioned at the approximate center of the detection surface of image detection device 20 or in the vicinity of a target area of subject 9. Radiation source 10 as shown by the dotted line in FIG. 1 shows said radiation source 10 in this state.

By the construction described above, imaging can always be performed in a state where the angle between the central axis L1a of the radiation and the detection surface is maintained perpendicular, and an image suitable for use in diagnosis can be obtained.

Next, the second embodiment of the radiation imaging system of the present invention will be described. FIG. 3 is a schematic view that shows the structure of the second embodiment of the radiation imaging system. The radiation imaging system of the second embodiment is a portable system of the type that adjusts the tilt of the central axis L1a of the radiation in relation to the radiation image detection device 20 so that it becomes perpendicular by changing the angle on the radiation image detection device 20 side, and with regard to this point, it differs from the first embodiment described above.

For this reason, instead of the tilt adjustment means 40 provided in the aforementioned first embodiment, the radiation imaging system 1 of the second embodiment is equipped with a tilt adjustment means 45 that changes the tilt angle of radiation image detection device 20 based on angular signal S or Sx and Sy, thereby making said tilt substantially perpendicular. The system 1 is further provided with a shift means 55 that enables horizontal movement of the radiation image detection device 20. The radiation source 10 is oriented so that the emission surface faces approximately straight down; that is, so that radiation L1 is emitted approximately straight downward.

As shown in FIG. 3, as the structure of the shift means 55, one is adopted which is capable of moving the image detection device in both the X and Y directions (the holding member 70 may be movable integrally with said device). As to the structure of the tilt adjustment means 45, one is adopted which is independently rotatable in the X and Y directions to enable tilting in both the X-Y planes. To this end, it does not matter what specific means are utilized. By such a structure, as in the first embodiment, the tilt of the central axis L1a of radiation L1 emitted from radiation source 10 in relation to the detection surface of image detection device 20 becomes adjustable, and the shift between said central axis L1a and the center of the subject 9 or the center of detection device 20 also becomes adjustable.

The angular signal detected by the angular signal output means 30 is input into tilt adjustment means 45. The tilt adjustment means 45 changes the tilt angle of the image detection device 20 based on said angular signal input thereto, thereby making substantially perpendicular the tilt of the radiation L1 in relation to the detection surface of the image detection device 20. Specifically, the image detection device is tilted to make the detection surface thereof approximately horizontal in relation to the radiation L1.

Note that with the construction of the second embodiment, even if the tilt angle of image detection device 20 is greatly changed, the amount of shift in the relative position between the central axis L1a of radiation L1 emitted from radiation source 10 and the radiation image detection device 20 or the subject 9 in the horizontal direction is small. Therefore it is thought that said horizontal shift virtually has no influence on image recording. However, in the case that this shift becomes a problem, the image detection device should be moved in the horizontal direction by the shift means 55.

FIG. 4 shows an example of a tilt adjustment means 45. As shown in the figure, an image detection device 20 composed of an image recording medium such as a stimulable phosphor sheet housed in a cassette is positioned on a holding member 70. The tilt adjustment means 45 is composed of tilt adjustment mechanisms (A1~A4 in the figure) that adjust the tilt of the image detection device 20 integrally with the holding member 70 by changing the amount of space between the holding member main body 71 and bottom plate 72 that compose said holding member 70. The tilt adjustment means 453 is housed in a case (for example, a cassette holder case) not shown in the figure, along with the image detection device 20, holding member main body 71, and the bottom plate 72, and provided underneath the subject 9. Note that the bottom plate 72 may also serve as a surface of said case.

With regard to the tilt adjustment mechanism, any may be utilized that is equipped with a mechanism that moves the image detection device 20 vertically integral with the holding member main body 71 by changing the amount of space between said main body 71 and bottom plate 72. For example, mechanisms that impart vertical motion via the rotation of a screw by a motor, or via geared teeth may be utilized. In FIG. 4, tilt adjustment mechanisms A1~A4 are provided in the four corners (four locations) in the space between holding member main body 71 and bottom plate 72. The heights of each tilt adjusting mechanism A1 through A4 are adjusted by a tilt data input portion (not shown) and a control portion (not shown) based on the detected tilt data.

FIG. 5 shows an example of a shift means 55. As shown in the figure, the shift means 55 is composed of: a shift mechanism Bx that moves holding member 70 which secures and holds image detection device 20 along mobile portion 56 which is capable of planar movement in the X-direction (left-right direction in the figure), and a shift mechanism By that moves said holding member 70 in the Y-direction (up-down direction in the figure). The mobile portion, which is capable of planar movement in the Y-direction, is not shown in the figure. The shift means 55 is structured to move the image detection device 20 integrally with the holding member 70 vertically and horizontally within a plane. With regard to the shift mechanisms Bx and By, any may be utilized that is equipped with a mechanism that moves holding member 70 in a planar fashion. For example, mechanisms that impart planar motion via screws or geared teeth as for the aforementioned tilt adjustment mechanism, may be utilized.

By the construction described above, imaging can always be performed in a state where the angle between the central axis L1a of the radiation and the detection surface is maintained perpendicular, and an image suitable for use in diagnosis can be obtained.

Figure 7:
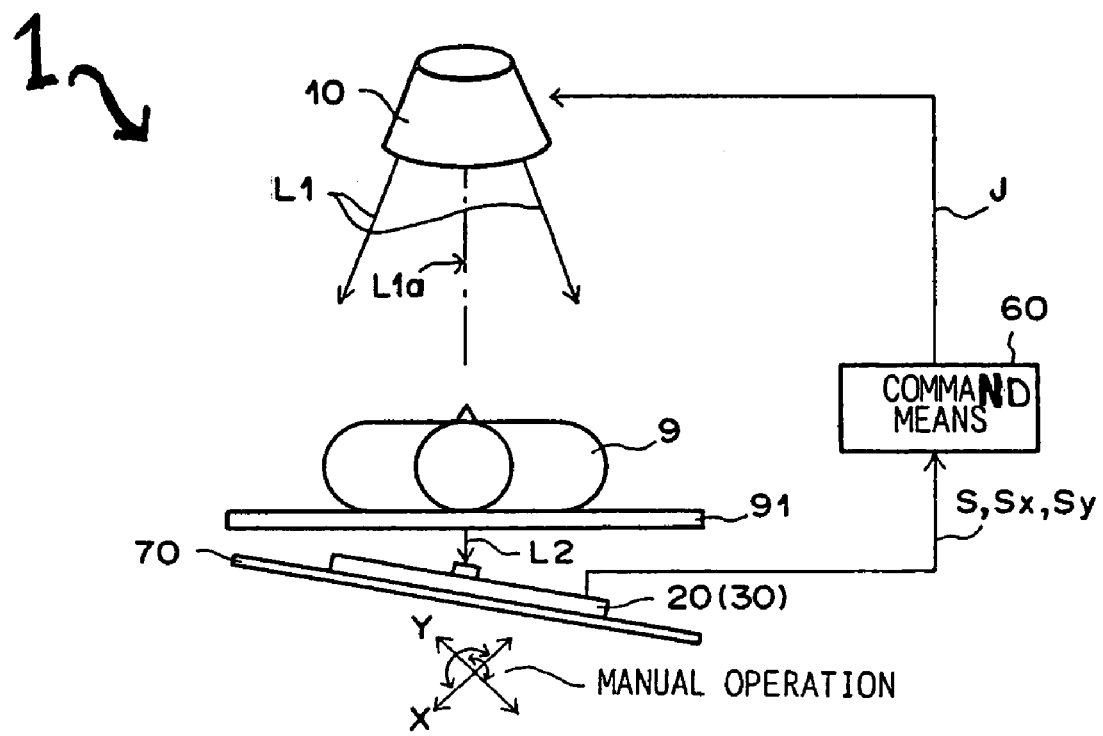
FIG. 7 is a schematic view that shows an alternate structure for the third embodiment of the radiation imaging system of the present invention.

Next, the third embodiment of the radiation imaging system of the present invention will be described. FIG. 6 and FIG. 7 are schematic views that show the structure of the third embodiment of the radiation imaging system. The radiation imaging system of the third embodiment is a portable system of the type that automatically emits radiation L1 from the radiation source 10 at a point when the tilt of the radiation L1 to be emitted therefrom in relation to the detection surface of the radiation image detection device 20 is substantially perpendicular, and with regard to this point, it differs from the first and second embodiments described above.

For this reason, the radiation imaging system of the third embodiment is equipped with a command means 60 that generates an exposure command to the radiation source 10 at a point when the tilt of the radiation L1 to be emitted therefrom in relation to the detection surface of the radiation image detection device 20 is substantially perpendicular. Note that this structure, in which the system is equipped with said command means 60, can be combined with the system of either the first or second embodiment.

The structure shown in FIG. 6 is an example of this, and it is the system of the second embodiment further provided with the command means 60. The structure shown in FIG. 7 is one in which the tilt of the radiation image detection device 20 is changed manually (by an operator) and, as stated above, generates an exposure command at a point when the tilt of the radiation L1 in relation to the detection surface becomes perpendicular. It need not be said that in the case that the structure shown in FIG. 7 is adopted, there is no necessity to equip means to adjust the tilt of radiation source 10 or image detection device 20. Note however, that even in this case, a portable shift means 50 that enables horizontal movement of the radiation source 10 may be provided.

In the case that the tilt on the radiation image detection device 20 side is to be manually changed as in the structure of FIG. 7, to avoid irradiation of the operator by radiation, the operator should perform said operation while wearing protective clothing, or the irradiation area of radiation should be focused.

As to the command means 60, a structure is adopted which monitors angular signal S or Sx and Sy output from the angular signal output means, and generates an exposure command J to the radiation source 10 when the tilt of the central axis L1a of radiation L1 in relation to the detection surface of the radiation image detection device 20 is substantially perpendicular. As to the determination for when said tilt is perpendicular, in the case that radiation source 10 is oriented so that its emission surface faces approximately straight downward, that is, so that radiation L1 is emitted approximately straight downward, the point in time when the detection surface of the image detection device is approximately level can be made the point of perpendicularity.

By the construction described above, imaging can always be performed in a state where the angle between the central axis L1a of the radiation and the detection surface is maintained perpendicular, and an image suitable for use in diagnosis can be obtained.

The preferred embodiments of the radiation imaging system and the radiation image detection device to be used with said system of the present invention have been described, but the present invention is not limited to the embodiments described above.

For example, in each of the embodiments described above, electronic levels integrally mounted on the radiation image detection device 20 were utilized as the angular signal output means 30. However, a projection sensor that utilizes light may be utilized as said means. In essence, any mechanism that is capable of measuring the angle formed by the central axis L1a of radiation L1 and the detection surface of the image detection device (incidence angle) may be adopted as the angular signal output means.

What is claimed is:

1. A portable radiation imaging system comprising:
   a radiation source; and
   a two dimensional radiation image detection device that records a radiation image by detecting the radiation emitted from said radiation source and is transmitted through a subject;
   wherein both of said radiation source and said two dimensional radiation image detection device are structured to be carriable, further comprising:
   an angular signal output means that outputs an angular signal which represents the degree of tilt of the radiation emitted from said radiation source in relation to the detection surface of said radiation image detection device; and
   a tilt adjustment means that adjusts said tilt of the radiation in relation to the detection surface of the radiation image detection device to become substantially perpendicular by changing the tilt angle of said radiation image detection device based on said angular signal output from said angular signal output means.

2. A radiation imaging system according to claim 1, wherein said image detection device comprises a stimulable phosphor sheet.

3. A radiation imaging system according to claim 1, wherein said image detection device is located at a distance from a subject being imaged.

4. A radiation imaging system according to claim 1, comprising a scattered ray removal grid board adjacent to the radiation image detection device which prevents the occurrence of false images and enhances image reproducibility after radiation has been transmitted through a subject.

5. A radiation imaging system according to claim 1, wherein said angular signal output means is an electronic level or a projection style angle sensor.

6. A radiation imaging system according to claim 1, further comprising a portable shift means that enables horizontal movement of the radiation source.

7. A radiation imaging system according to claim 1, further comprising a portable shift means that enables horizontal movement of the radiation image detection device.

8. The system of claim 1, wherein the angular sensor output means comprises an electronic level.

9. The system of claim 1, wherein the tilt angle is obtained without using the radiation emitted from the radiation source.

10. The system according to claim 1, wherein said radiation source and said two dimensional radiation image detection device are carriable so as to be easily transported to a location outside of a hospital.

11. The system according to claim 1, wherein said radiation source comprises an x-ray source.

12. A portable radiation imaging system comprising:
    a radiation source; and
    a two dimensional radiation image detection device that records a radiation image by detecting the radiation emitted from said radiation source and is transmitted through a subject;
    wherein both of said radiation source and said two dimensional radiation image detection device are structured to be carriable, further comprising;
    a command means that generates an exposure command to said radiation source when a tilt of the radiation to be emitted from said radiation source in relation to the detection surface of said radiation image detection device is substantially perpendicular.

13. A radiation imaging system according to claim 12, wherein said image detection device comprises a stimulable phosphor sheet.

14. A radiation imaging system according to claim 12, wherein said image detection device is located at a distance from a subject being imaged.

15. A radiation imaging system according to claim 12, comprising a scattered ray removal grid board adjacent to the radiation image detection device which prevents the occurrence of false images and enhances image reproducibility after radiation has been transmitted through a subject.

16. A portable radiation imaging system according to claim 12, further comprising:
    an angular signal output means that outputs an angular signal which represents the degree of tilt of the radiation emitted from said radiation source in relation to the detection surface of said radiation image detection device.

17. A portable radiation imaging system according to claim 16, wherein said angular signal output means is an electronic level or a projection style angle sensor.

18. A radiation imaging system according to claim 12, further comprising a portable shift means that enables horizontal movement of the radiation source.

19. A radiation imaging system according to claim 12, further comprising a portable shift means that enables horizontal movement of the radiation image detection device.

20. The radiation imaging system according to claim 12, further comprising means for determining a perpendicular orientation between the detection device and output of rays by the radiation source,
    wherein upon generation of the exposure command, the radiation source automatically emits radiation.

21. A two dimensional radiation image detection device recording a radiation image equipped with an angular signal output means that outputs an angular signal which represents the degree of tilt of the radiation emitted from a radiation source in relation to the detection surface of said radiation image detection device.

22. A radiation image detection device according to claim 21, wherein said device is portable.

23. A radiation image detecting device according to claim 21, wherein said image detection device comprises a stimulable phosphor sheet.

24. A radiation image detecting device according to claim 21, wherein said image detection device is located at a distance from a subject being imaged.

25. A radiation image detecting device according to claim 21, comprising a scattered ray removal grid board adjacent to the radiation image detection device which prevents the occurrence of false images and enhances image reproducibility after radiation has been transmitted through a subject.

26. A radiation image detecting device according to claim 21, wherein said angular signal output means is an electronic level or a projection style angle sensor.

27. A radiation image detection device according to claim 21, wherein said device is carriable.

28. A two dimensional radiation image detection device recording a radiation image equipped with a command means that generates an exposure command to a radiation source when the tilt of the radiation to be emitted by the radiation source in relation to the detection surface of said radiation image detection device is substantially perpendicular.

29. A radiation image detection device according to claim 28, wherein said device is portable.

30. A radiation image detecting device according to claim 28, wherein said image detection device comprises a stimulable phosphor sheet.

31. A radiation image detecting device according to claim 28, wherein said image detection device is located at a distance from a subject being imaged.

32. A radiation image detecting device according to claim 28, comprising a scattered ray removal grid board adjacent to the radiation image detection device which prevents the occurrence of false images and enhances image reproducibility after radiation has been transmitted through a subject.

33. A radiation image detection device according to claim 28, wherein said device is carriable.

34. A two dimensional radiation image detection device according to claim 28, further comprising:
   a two dimensional radiation image detection device that records a radiation image by detecting the radiation emitted from the radiation source and is transmitted through a subject.

* * * * *